United States Patent
Koerber

(10) Patent No.: US 10,349,593 B2
(45) Date of Patent: Jul. 16, 2019

(54) SPINACH VARIETY NUN 05004 SPS

(71) Applicant: Nunhems B.V., AB Nunhem (NL)

(72) Inventor: Frederike Koerber, AB Nunhem (NL)

(73) Assignee: NUNHEMS B.V., Nunhem (NL)

( * ) Notice: Subject to any disclaimer, the term of this patent is extended or adjusted under 35 U.S.C. 154(b) by 0 days.

(21) Appl. No.: 15/831,908

(22) Filed: Dec. 5, 2017

(65) Prior Publication Data

US 2018/0098518 A1    Apr. 12, 2018

Related U.S. Application Data

(60) Provisional application No. 62/531,371, filed on Jul. 12, 2017.

(51) Int. Cl.
*A01H 5/12*    (2018.01)
*A01H 6/02*    (2018.01)

(52) U.S. Cl.
CPC .............. *A01H 5/12* (2013.01); *A01H 6/028* (2018.05)

(58) Field of Classification Search
None
See application file for complete search history.

(56) References Cited

U.S. PATENT DOCUMENTS

2013/0055456 A1\*  2/2013  den Braber ............... A01H 5/12 800/260

FOREIGN PATENT DOCUMENTS

| WO | 2013182646 A1 | 12/2013 |
| WO | 2014076249 A1 | 5/2014 |

OTHER PUBLICATIONS

UPOV, *Spinacia oleracea* L. Guidelines (2016).\*
Ren, Yan, et al., Shoot regeneration and ploidy variation in tissue culture of honeydew melon (*Cucumis melo* L. inodorus), In Vitro Cell. Dev. Biol. Plant, 2013, pp. 223-229, vol. 49.
Colijn-Hooymans, C.M., et al., Competence for regeneration of cucumber cotyledons is restricted to specific developmental stages, Plant Cell, Tissue and Organ Culture, 1994, pp. 211-217, vol. 39.
JPOV, Spinach; Guidelines for the Conduct of Tests for Distinctness, Uniformity and Stability, TG55/7 (Geneva, last revised 2016), upov.int/ under edocs/tgdocs/en/tg055.pdf, pp. 1-3.
Objective description of Variety Spinach *Spinacia oleracea* L.), ST-470-83 the US Department of Agriculture, Agricultural Marketing Service, Plant Variety Protection Office, Beltsville, MD 20705; Updated Jun. 2015; available on the world wide web at ams.usda.gov/ under sites/default/files/media/83-Spinach%20ST-470-83% 202015.pdf.
Vos, Pieter, et al., AFLP: a new technique for DNA fingerprinting, Nucleic Acids Research, 1995, pp. 4407-4414, vol. 23, No. 21.
Parvathaneni, Rajiv Krishna, et al., Fingerprinting in Cucumber and Melon (*Cucumis* spp.) Genotypes Using Morphological and ISSR Markers, J. Crop Sci. Biotech., 2011 (Mar.), pp. 39-43, vol. 14, No. 1.
Brotman, Y., et al., Resistance gene homologues in melon are linked to genetic loci conferring disease and pest resistance, Theor Appl Genet, 2002, pp. 1055-1063, vol. 104.
Wijnker, Erik, et al., Hybrid recreation by reverse breeding in *Arabidopsis thaliana*, Nature Protocols, 2014, pp. 761-772, vol. 9, DOI: doi:10.1038/nprot.2014.049.

\* cited by examiner

*Primary Examiner* — Russell T Boggs
(74) *Attorney, Agent, or Firm* — Arent Fox LLP

(57) ABSTRACT

The invention provides a new and distinct hybrid variety of Spinach, NUN 05004 SPS as well as seeds and plants and leaves thereof.

19 Claims, No Drawings

SPINACH VARIETY NUN 05004 SPS

CROSS REFERENCE TO RELATED APPLICATION

This application claims the benefit of U.S. Patent Application No. 62/531,371, filed Jul. 12, 2017, the contents of which are herein incorporated by reference in their entirety.

FIELD OF THE INVENTION

The present invention relates to the field of plant breeding and, more specifically, to the development of NUN 05004 SPS (also designated as NUN 05004 or NUN 05004 F1 or NUN 05004 hybrid) or Alcor. The invention further relates to vegetative reproductions of NUN 05004 SPS, methods for tissue culture of NUN 05004 SPS and regenerating a plant from such a tissue culture and also to phenotypic variants of NUN 05004 SPS.

The goal of vegetable breeding is to combine various desirable traits in a single variety/hybrid. Such desirable traits may include greater yield, resistance to diseases, insects or other pests, tolerance to heat and drought, better agronomic quality, higher nutritional value, enhanced growth rate and improved leaf properties.

Breeding techniques take advantage of a plant's method of pollination. There are two general methods of pollination: a plant self-pollinates if pollen from one flower is transferred to the same or another flower of the same genotype. A plant cross-pollinates if pollen comes to it from a flower of a different genotype.

Plants that have been self-pollinated and selected for (uniform) type over many generations become homozygous at almost all gene loci and produce a uniform population of true breeding progeny of homozygous plants. A cross between two such homozygous plants of different lines produces a uniform population of hybrid plants that are heterozygous for many gene loci. The extent of heterozygosity in the hybrid is a function of the genetic distance between the parents. Conversely, a cross of two plants each heterozygous at a number of loci produces a segregating population of hybrid plants that differ genetically and are not uniform. The resulting non-uniformity makes performance unpredictable.

The development of uniform varieties requires the development of homozygous inbred plants, the crossing of these inbred plants to make hybrids, and the evaluation of the hybrids resulting from the crosses. Pedigree breeding and recurrent selection are examples of breeding methods that have been used to develop inbred plants from breeding populations. Those breeding methods combine the genetic backgrounds from two or more plants or various other broad-based sources into breeding pools from which new lines are developed by selfing and selection of desired phenotypes. The new plants are evaluated to determine which have commercial potential. One crop species which has been subject to such breeding programs and is of particular value is spinach.

Spinach (*Spinacia oleracea*) is a flowering plant in the family Amaranthaceae. Spinach is an annual plant (rarely biennial) having flowers that mature into a small hard dry lumpy fruit cluster about 5-10 mm across containing several seeds.

Spinach has two stages in its life cycle including the vegetative, rosette stage in which the plant is marketable (about 35-40 days) and the bolting, seed stalk stage in which the plant is no longer marketable. Spinach can grow in a range of soils as long as they are moist and fertile, and particularly sandy loams that are high in organic matter.

While breeding efforts to date have provided a number of useful spinach lines with beneficial traits, there remains a great need in the art for new varieties with further improved traits. Such plants would benefit farmers and consumers alike by improving crop yields and/or quality.

SUMMARY OF THE INVENTION

In an aspect of the invention, a seed of Spinach variety NUN 05004 SPS is provided, wherein a representative sample of said seed has been deposited under Accession Number NCIMB 43376. The invention also provides for a plurality of seeds of NUN 05004 SPS. The Spinach seed of NUN 05004 SPS may be provided as an essentially homogeneous population of Spinach seed. Therefore, seed of the invention may be defined as forming at least about 97% of the total seed, including at least about 98%, 99% or more of the seed. The population of seed of NUN 05004 SPS may be particularly defined as being essentially free from other seed. The seed population may be grown into plants to provide an essentially homogeneous population of Spinach plants according to the invention.

Also encompassed is a plant grown from a seed of Spinach variety NUN 05004 SPS and a plant part thereof. In another aspect the invention provides for a hybrid variety of Spinach called NUN 05004 SPS. The invention also provides for a progeny of NUN 05004 SPS. Especially, a plant or a progeny retaining all or all but one, two or three of the "distinguishing characteristics" or all or all but one, two or three of the "morphological and physiological characteristics" of NUN 05004 SPS referred to herein, is encompassed herein as well as methods for producing that plant or progeny.

In one aspect, a plant or a progeny of the invention have all the physiological and morphological characteristics of variety NUN 05004 SPS when grown under the same environmental conditions. In another aspect such a plant or such progeny have all or all but one, two or three of the physiological and morphological characteristics of NUN 05004 SPS when measured under the same environmental conditions and evaluated at significance levels of 1%, 5% or 10% significance (which can also be expressed as a p-value) wherein a representative sample of seed of variety NUN 05004 SPS has been deposited under Accession Number NCIMB 43376. In a second aspect, a plant or a progeny of the invention have all the physiological and morphological characteristics of variety NUN 05004 SPS when grown under the same environmental conditions. In another aspect such a plant or such progeny have all or all but one, two or three of the physiological and morphological characteristics as listed in Table 1 and/or 2 for variety NUN 05004 SPS when measured under the same environmental conditions and evaluated at significance levels of 1%, 5% or 10% significance.

In another aspect a plant of NUN 05004 SPS or said progeny plants has 7, 8, or more or all of the distinguishing characteristics: 1) Leaf shape (prime market stage); 2) Leaf blade size type (prime market stage); 3) Leaf petiole length to blade (prime market stage); 4) Leaf petiole length type (prime market stage); 5) Seedling Cotyledon length; 6) Start of bolting; 7) Height of seed stalk; 8) Plant habit (prime market stage); 9 Plant spread (prime market stage); and 10) Plant height (prime market stage). NUN 05004 SPS is a fresh market Spinach and suitable for growing during summer, spring and autumn.

Also a plant part obtained from variety NUN 05004 SPS is provided, wherein said plant part is selected from the group consisting of: a fruit, a harvested fruit, a part of a fruit, a leaf, a part of a leaf, pollen, an ovule, a cell, a petiole, a shoot or a part thereof, a stem or a part thereof, a root or a part thereof, a root tip, a cutting, a seed, a part of a seed, seed coat or another maternal tissue which is part of a seed grown on said varieties, hypocotyl, cotyledon, a scion, a stock, a rootstock, a pistil, an anther, and a flower or a part thereof. Leaves are particularly important plant parts. In a further embodiment, the plant part obtained from variety NUN 05004 SPS is a cell, optionally a cell in a cell or tissue culture. That cell may be grown into a plant of NUN 05004 SPS.

The invention also provides a cell culture of NUN 05004 SPS and a plant regenerated from NUN 05004 SPS, which plant has all the characteristics of NUN 05004 SPS when grown under the same environmental conditions, as well as methods for regenerating NUN 05004 SPS. Alternatively, a regenerated plant may have one characteristic that is different from NUN 05004 SPS.

Further, a vegetatively propagated plant of variety NUN 05004 SPS is provided having all or all but one, two or three of the morphological and physiological characteristics NUN 05004 SPS when grown under the same environmental conditions.

Further, a Spinach leaf produced on a plant grown from a seed of NUN 05004 SPS is provided.

In still another aspect, a seed growing or grown on a plant of NUN 05004 SPS is provided (i.e. produced after pollination of the flower of NUN 05004 SPS).

Definitions

All patent and non-patent documents cited herein are incorporated by reference in their entirety "Spinach" refers herein to plants of the species *Spinacia oleracea*, and a leaf or leaves thereof. The most commonly eaten part of a spinach is the leaf.

"Cultivated Spinach" refers to plants of *Spinacia oleracea* L, i.e. varieties, breeding lines or cultivars of the species *Spinacia oleracea* L, cultivated by humans and having good agronomic characteristics; preferably such plants are not "wild plants", i.e. plants which generally have much poorer yields and poorer agronomic characteristics than cultivated plants and e.g. grow naturally in wild populations. "Wild plants" include for example ecotypes, PI (Plant Introduction) lines, landraces or wild accessions or wild relatives of a species.

The terms "Spinach plant designated NUN 05004 SPS", "NUN 05004 SPS", "NUN 05004", "NUN 05004 F1", "05004 SPS" or "Spinach 05004" are used interchangeably herein and refer to a Spinach plant of variety NUN 05004 SPS, representative seed of which having been deposited under Accession Number NCIMB 43376.

A "seed of NUN 05004 SPS" refers to a Spinach seed which can be grown into a plant of NUN 05004 SPS wherein a representative sample of viable seed of NUN 05004 SPS has been deposited under Accession Number NCIMB 43376. A seed can be in any stage of maturity, for example a mature, viable seed, or an immature, non-viable seed. A seed comprises an embryo and maternal tissues.

An "embryo of NUN 05004 SPS" refers to an F1 hybrid embryo as present in a seed of NUN 05004 SPS, a representative sample of said seed of NUN 05004 SPS having been deposited under Accession Number NCIMB 43376.

A "seed grown on NUN 05004 SPS" refers to a seed grown on a mature plant of NUN 05004 SPS or inside a fruit of NUN 05004 SPS. The "seed grown on NUN 05004 SPS" contains tissues and DNA of the maternal parent, NUN 05004 SPS. The "seed grown on NUN 05004 SPS" contains an F2 embryo. When said seed is planted, it grows into a first generation progeny plant of NUN 05004 SPS.

"Tissue culture" or "cell culture" refers to a composition comprising isolated cells of the same or a different type or a collection of such cells organized into parts of a plant. Tissue culture of various tissues of cucumber and regeneration of plants therefrom is well known and widely published (see, e.g., Ren et al., In Vitro Cell. Dev. Biol.—Plant (2013) 49:223-229; Colijn-Hooymans (1994), Plant Cell, Tissue and Organ Culture 39: 211-217). Similarly, the skilled person is well-aware how to prepare a "tissue culture" or "cell culture".

"UPOV descriptors" are the plant variety descriptors described for cucumber in the "Guidelines for the Conduct of Tests for Distinctness, Uniformity and Stability, TG104/5 (Geneva, last revised 2016), as published by UPOV (International Union for the Protection of New Varieties and Plants, available on the world wide web at upov.int) and which can be downloaded from the world wide web at upov.int/under edocs/tgdocs/en/tg061.pdf and is herein incorporated by reference in its entirety.

"USDA descriptors" are the plant variety descriptors described for spinach in the "Objective description of Variety Spinach *Spinacia oleracea* L.)", ST-470-83 as published by the US Department of Agriculture, Agricultural Marketing Service, Plant Variety Protection Office, Beltsville, Md. 20705 and which can be downloaded from the world wide web at ams.usda.gov/under sites/default/files/media/83-Spinach %20ST-470-83%202015.pdf. "Non-USDA descriptors" are other descriptors suitable for describing Spinach.

"RHS" refers to the Royal Horticultural Society of England which publishes an official botanical color chart quantitatively identifying colors according to a defined numbering system. The chart may be purchased from Royal Horticulture Society Enterprise Ltd RHS Garden; Wisley, Woking; Surrey GU236QB, UK, e.g., the RHS color chart: 2007 (The Royal Horticultural Society, charity No: 222879, PO Box 313 London SW1P2PE.

As used herein and except as otherwise indicated, the term "plant" includes the whole plant or any part thereof, preferably having the same genetic makeup as the plant from which it is obtained, such as a plant organ (e.g. harvested or non-harvested fruits), a plant cell, a plant protoplast, a plant cell tissue culture or a tissue culture from which a whole plant can be regenerated, a plant cell that is intact in a plant, a clone, a micropropagation, plant callus, a plant cell clump, a plant transplant, a vegetative propagation, a seedling, or parts of a plant (e.g. harvested tissues or organs), such as a fruit, a harvested fruit, a part of a fruit, a leaf, a part of a leaf, pollen, an ovule, an embryo, a petiole, a shoot or a part thereof, a stem or a part thereof, a root or a part thereof, a root tip, a cutting, a seed, a part of a seed, seed coat or another maternal tissue which is part of a seed grown on a variety of the invention, hypocotyl, cotyledon, a scion, a graft, a stock, a rootstock, a pistil, an anther, and a flower or parts of any of these and the like. Also any developmental stage is included, such as seedlings, cuttings prior or after rooting, mature plants or leaves. Alternatively, a plant part may also include a plant seed which comprises one or two sets of chromosomes derived from the parent plant, e.g. from NUN 05004 SPS. An F2 progeny produced from self-pollination of NUN 05004 SPS will thus comprise two sets of chromosomes derived from NUN 05004 SPS, while an F2 progeny derived from cross-fertilization of NUN 05004 SPS will comprise only one set of chromosomes from NUN 05004 SPS and the other set of chromosomes from the other parent.

"Harvested plant material" refers herein to plant parts (e.g. leaves detached from the whole plant) which have been collected for further storage and/or further use. Preferably, leaves are harvested at harvest maturity or prime market stage. In another embodiment, babyleaves are harvested.

"Reference Variety" or "check variety" refers herein to variety Antalia, a commercial variety from company Nunhems, which has been planted in a trial together with NUN 05004 SPS. USDA descriptors of NUN 05004 SPS were compared to the USDA descriptors of Antalia.

A plant having "all the physiological and morphological characteristics" of a referred-to-plant means a plant showing the physiological and morphological characteristics of the referred-to-plant when grown under the same environmental conditions, preferably in the same experiment; the referred-to-plant can be a plant from which it was derived, e.g. the progenitor plant, the parent, the recurrent parent, the plant used for tissue- or cell culture, etc. A physiological or morphological characteristic can be a numerical characteristic or a non-numerical characteristic. In one aspect, a plant has "all but one, two or three of the physiological and morphological characteristics" of a referred-to-plant, or "all the physiological and morphological characteristics" of Table 1 and/or 2 or "all or all but one, two or three of the physiological and morphological characteristics" of Table 1 and/or 2.

The physiological and/or morphological characteristics mentioned above are commonly evaluated at significance levels of 1%, 5% or 10% if they are numerical, or for having an identical degree (or type) if not numerical, if measured under the same environmental conditions. For example, a progeny plant or a Single Locus Converted plant or a mutated plant of NUN 05004 SPS may have one or more (or all) of the essential physiological and/or morphological characteristics of said variety listed in Table 1 and/or 2, as determined at the 5% significance level (i.e. $p<0.05$) when grown under the same environmental conditions.

"Distinguishing characteristics" or "distinguishing morphological and/or physiological characteristics" refers herein to the characteristics which distinguish (i.e. are different) between the new variety and other Spinach varieties, such as the Reference Variety, when grown under the same environmental conditions. The distinguishing characteristics between NUN 05004 SPS and Reference Variety are described elsewhere herein and also can be seen in Table 1 and/or Table 2. When comparing NUN 05004 SPS with different varieties, the distinguishing characteristics will be different. In one aspect, the distinguishing characteristics may therefore include at least one, two, three or more (or all) of the characteristics listed in Table 1 and/or 2. All numerical distinguishing characteristics are statistically significantly different at $p<0.05$ between NUN 05004 SPS and the other variety, e.g. Reference Variety.

NUN 05004 SPS has the following distinguishing characteristics when compared to the Reference Variety: 1) Leaf shape (prime market stage); 2) Leaf blade size type (prime market stage); 3) Leaf petiole length to blade (prime market stage); 4) Leaf petiole length type (prime market stage); 5) Seedling Cotyledon length; 6) Start of bolting; 7) Height of seed stalk; 8) Plant habit (prime market stage); 9 Plant spread (prime market stage); and 10) Plant height (prime market stage). This can be seen in a.m. Table 1, where the USDA characteristics of NUN 05004 SPS are compared to the characteristics of Reference Variety, when grown under the same environmental conditions Thus, a Spinach plant "comprising the distinguishing characteristics of NUN 05004 SPS (such as a progeny plant) refers herein to a plant which does not differ significantly from said variety in the distinguishing characteristics above. Therefore in one aspect a plant (such as a progeny plant of NUN 05004 SPS) is provided which does not differ significantly from NUN 05004 SPS in the distinguishing characteristics above.

Similarity and differences between two different plant lines or varieties can be determined by comparing the number of morphological and/or physiological characteristics (e.g. the characteristics as listed in Table 1 and/or 2) that are the same (i.e. statistically not significantly different) or that are different (i.e. statistically significantly different) between the two plant lines or varieties when grown under the same environmental conditions. A numerical characteristic is considered to be "the same" when the value for a numeric characteristic is not significantly different at the 1% ($p<0.01$) or 5% ($p<0.05$) significance level, using one way Analysis of variance (ANOVA), a standard method known to the skilled person. Non-numerical or "degree" or "type" characteristic are considered "the same" when the values have the same "degree" or "type" when scored using USDA and/or UPOV descriptors, if the plants are grown under the same environmental conditions.

As used herein, the term "variety", "cultivated Spinach" or "cultivar" means a plant grouping within a single botanical taxon of the lowest known rank, which grouping, irrespective of whether the conditions for the grant of a breeder's right are fully met, can be defined by the expression of the characteristics resulting from a given genotype or combination of genotypes, distinguished from any other plant grouping by the expression of at least one of the said characteristics and considered as a unit with regard to its suitability for being propagated unchanged.

A "plant line" is for example a breeding line which can be used to develop one or more varieties. A breeding line is typically highly homozygous.

"Hybrid variety" or "F1 hybrid" refers to the seeds harvested from crossing two inbred (nearly homozygous) parental lines. For example, the female parent is pollinated with pollen of the male parent to produce hybrid (F1) seeds on the female parent.

"Regeneration" refers to the development of a plant from cell culture or tissue culture or vegetative propagation.

"Vegetative propagation", "vegetative reproduction" or "clonal propagation" are used interchangeably herein and mean a method of taking a part of a plant and allowing that plant part to form at least roots, and also refer to the plant or plantlet obtained by that method. Optionally, the vegetative propagation is grown into a mature plant. The skilled person is aware of what plant parts are suitable for use in the method.

"Selfing" refers to self-pollination of a plant, i.e., the transfer of pollen from the anther to the stigma of the same plant.

"Crossing" refers to the mating of two parent plants. The term encompasses "cross-pollination" and "selfing".

"Cross-pollination" refers to the fertilization by the union of two gametes from different plants.

"Yield" means the total weight of all Spinach leaves harvested per hectare of a particular line or variety. It is understood that "yield" expressed as weight of all Spinach fruits harvested per hectare can be obtained by multiplying the number of plants per hectare times the "yield per plant". "Marketable yield" means the total weight of all marketable Spinach leaves, especially leaves that are not damaged or diseased, harvested per hectare of a particular line or variety.

As used herein, the terms "resistance" and "tolerance" are used interchangeably to describe plants that show no symptoms or significantly reduced symptoms to a specified biotic pest, pathogen, abiotic influence or environmental condition compared to a susceptible plant. These terms are optionally also used to describe plants showing some symptoms but that are still able to produce marketable product with an acceptable yield.

The term "traditional breeding techniques" encompasses herein crossing, selfing, selection, doubled haploid production, embryo rescue, protoplast fusion, marker assisted selection, mutation breeding etc. as known to the breeder (i.e. methods other than genetic modification/transformation/transgenic methods), by which, for example, a genetically heritable trait can be transferred from one Spinach line or variety to another. It optionally includes epigenetic modifications.

"Backcrossing" is a traditional breeding technique used to introduce a trait into a plant line or variety. The plant containing the trait is called the donor plant and the plant into which the trait is transferred is called the recurrent parent. An initial cross is made between the donor parent and the recurrent parent to produce a progeny plant. Progeny plants which have the trait are then crossed to the recurrent parent. After several generations of backcrossing and/or selfing the recurrent parent comprises the trait of the donor. The plant generated in this way may be referred to as a "single trait converted plant". The technique can also be used on a parental line of a hybrid.

"Progeny" as used herein refers to a plant obtained from a plant designated NUN 05004 SPS. A progeny may be obtained by regeneration of cell culture or tissue culture or parts of a plant of said variety or selfing of a plant of said variety or by producing seeds of a plant of said variety. In further embodiments, progeny may also encompass plants obtained from crossing of at least one plant of said variety with another Spinach plant of the same variety or another variety or (breeding) line, or with wild Spinach plants. A progeny may comprise a mutation or a transgene. A first generation progeny" or is the progeny directly derived from, obtained from, obtainable from or derivable from the parent plant by, e.g., traditional breeding methods (selfing and/or cross-pollinating) or regeneration. Thus, a plant of NUN 05004 SPS is the male parent, the female parent or both of a first generation progeny of NUN 05004 SPS. Progeny may have all the physiological and morphological characteristics of variety NUN 05004 SPS when grown under the same environmental conditions and/or progeny may have (be selected for having) one or more of the distinguishing characteristics of cucumber of the invention. Using common breeding methods such as backcrossing or recurrent selection, one or more specific characteristics may be introduced into said variety, to provide or a plant comprising all but 1, 2, or 3 or more of the morphological and physiological characteristics of NUN 05004 SPS (as listed in Table 1 and/or 2)

The terms "gene converted" or "conversion plant" or "single locus converted plant" in this context refer to Spinach plants which are developed by backcrossing wherein essentially all of the desired morphological and physiological characteristics of the parent variety or line are recovered, in addition to the one or more genes transferred into the parent via the backcrossing technique (optionally including reverse breeding or reverse synthesis of breeding lines) or via genetic engineering or through mutation breeding. Likewise a "Single Locus Converted (Conversion) Plant" refers to plants which are developed by plant breeding techniques comprising or consisting of mutation and/or by genetic transformation and/or by backcrossing, wherein essentially all of the desired morphological and physiological characteristics of a Spinach variety are recovered in addition to the characteristics of the single locus having been transferred into the variety via the backcrossing technique. In case of a hybrid, the gene may be introduced in the male or female parental line.

"Marker" refers to a readily detectable phenotype, preferably inherited in codominant fashion (both alleles at a locus in a diploid heterozygote are readily detectable), with no environmental variance component, i.e., a heritability of 1.

"Average" refers herein to the arithmetic mean.

The term "mean" refers to the arithmetic mean of several measurements. The skilled person understands that the appearance of a plant depends to some extent on the growing conditions of said plant. Thus, the skilled person will know typical growing conditions for Spinach described herein. The mean, if not indicated otherwise within this application, refers to the arithmetic mean of measurements on at least 10 different, randomly selected plants of a variety or line.

DETAILED DESCRIPTION

The present invention relates to a plant of NUN 05004 SPS wherein a representative sample of seeds of said variety was deposited under the Budapest Treaty, with Accession number NCIMB 43376.

The present invention also relates to a seed of Spinach variety, referred to as NUN 05004 SPS, wherein a representative sample of said seed was deposited under the Budapest Treaty, with Accession number NCIMB 43376.

In another aspect, the invention provides for a Spinach plant part of variety NUN 05004 SPS, preferably a leaf, a representative sample of seed from said variety has been deposited under the Budapest Treaty, with Accession number NCIMB 43376.

A seed of hybrid variety NUN 05004 SPS is obtainable by crossing the male parent of said variety with the female parent of said variety and harvesting the seeds produced on the female parent. The resultant seeds of said variety can be grown to produce plants of said variety. In one embodiment a seed or a plurality of seeds of said variety are packaged into a container of any size or type (e.g., bags, cartons, cans, etc.). The seed may be disinfected, primed and/or treated with various compounds, such as seed coatings or crop protection compounds. The seed produces a plant of NUN 05004 SPS.

Also provided is a plant of Spinach variety NUN 05004 SPS, or a leaf or other plant part thereof, produced from a seed, wherein a representative sample of said seeds has been deposited under the Budapest Treaty, with Accession Number NCIMB 43376.

Also a plant part obtained from variety NUN 05004 SPS is provided, wherein said plant part is selected from the group consisting of: a fruit, a harvested fruit, a part of a fruit, a leaf, a part of a leaf, pollen, an ovule, a cell, a petiole, a shoot or a part thereof, a stem or a part thereof, a root or a part thereof, a root tip, a cutting, a seed, a part of a seed, seed coat or another maternal tissue which is part of a seed grown on said varieties, hypocotyl, cotyledon, a scion, a stock, a rootstock, a pistil, an anther, and a flower or a part thereof.

Leaves are particularly important plant parts. In a further embodiment, the plant part obtained from variety NUN 05004 SPS is a cell, optionally a cell in a cell or tissue culture. That cell may be grown into a plant of NUN 05004 SPS. A part of a variety of the invention, i.e. NUN 05004 SPS (or of progeny NUN 05004 SPS or of a plant having all physiological and/or morphological characteristics but one, two or three which are different from those of NUN 05004 SPS) further encompasses any cells, tissues, organs obtainable from the seedlings or plants in any stage of maturity.

The invention also provides for a food or feed product or a processed product comprising or consisting of a plant part described herein wherein the plant part can be identified as a part of the plant of the invention. Preferably, the plant part is a Spinach leaf or part thereof and/or an extract from a leaf or another plant part described herein comprising at least one cell of NUN 05004 SPS. The food or feed product may be fresh or processed, e.g., dried, grinded, powdered, pickled, chopped, cooked, roasted, in a sauce, in a sandwich, pasted, puréed or concentrated, juiced, pickled, canned, steamed, boiled, fried, blanched and/or frozen, etc.

Such a plant part of NUN 05004 SPS can be stored and/or processed further. Encompassed are therefore also food or feed products comprising one or more of such parts, such as canned, chopped, cooked, roasted, in a sauce, in a sandwich, pasted, puréed or concentrated, juiced, frozen, dried, pickled, or powdered Spinach leaf from NUN 05004 SPS or from progeny of said varieties, or from a derived variety, such as a plant having all but one, two or three physiological and/or morphological characteristics of NUN 05004 SPS.

In a preferred embodiment, the invention provides for a Spinach leaf of variety NUN 05004 SPS, or a part of a leaf of said varieties. The leaf can be in any stage of maturity, for example immature or mature. In another embodiment, the invention provides for a container comprising or consisting of a plurality of harvested Spinach leaves or parts of leaves of said variety, or leaves of progeny thereof, or leaves of a derived variety.

In another embodiment the plant, plant part or seed of NUN 05004 SPS is inside a container, For example, containers such as cans, boxes, crates, bags, cartons, Modified Atmosphere Packaging, films (e.g. biodegradable films), etc. comprising a plant or a part of a plant (fresh and/or processed) of NUN 05004 SPS or a seed of NUN 05004 SPS are also provided herein. In a preferred embodiment, the container comprises a plurality of seeds of NUN 05004 SPS, or a plurality of plant parts of NUN 05004 SPS.

The present invention further relates to a Spinach variety, referred to as NUN 05004 SPS, which—when compared to its REFERENCE VARIETY Antalia—has the following distinguishing characteristics: 1) Leaf shape (prime market stage); 2) Leaf blade size type (prime market stage); 3) Leaf petiole length to blade (prime market stage); 4) Leaf petiole length type (prime market stage); 5) Seedling Cotyledon length; 6) Start of bolting; 7) Height of seed stalk; 8) Plant habit (prime market stage); 9 Plant spread (prime market stage); and 10) Plant height (prime market stage), where the characteristics are determined at the 5% significance level for plants grown under the same environmental conditions. Also encompassed by the present invention are parts of that plant.

In one embodiment a plant of NUN 05004 SPS or a progeny plant thereof, comprises all of the following morphological and/or physiological characteristics (i.e. average values of distinguishing characteristics, as indicated on the USDA Objective description of variety—Spinach (unless indicated otherwise)): 1) Leaf shape (prime market stage); 2) Leaf blade size type (prime market stage); 3) Leaf petiole length to blade (prime market stage); 4) Leaf petiole length type (prime market stage); 5) Seedling Cotyledon length; 6) Start of bolting; 7) Height of seed stalk; 8) Plant habit (prime market stage); 9 Plant spread (prime market stage); and 10) Plant height (prime market stage), where the characteristics are determined at the 5% significance level for plants grown under the same environmental conditions. An example of values for the distinguishing characteristics collected in a trial run according to UDSA requirements can be found in Table 1. A part of this plant is also provided.

In another embodiment hybrid NUN 05004 SPS has resistance to *Peronospora farinosa* race 1-16 that is 9 (present) measured according to UPOV standards.

The invention further provides a Spinach plant which does not differ from the plant of claim 1 as determined at the 1%, 2%, 3%, 4% or 5% significance level when grown under the same environmental conditions. Thus the plants are measured in the same trial. Preferably, the trial is conducted as recommended by the USDA or UPOV. The invention also comprises a part of said plant The invention also provides a tissue or cell culture comprising cells of NUN 05004 SPS. Such a tissue culture can for example be grown on plates or in liquid culture, or be frozen for long term storage. The cells of NUN 05004 SPS used to start the culture can be selected from any plant part suitable for vegetative reproduction, or in a preferred embodiment can be selected from embryos, meristems, cotyledons, hypocotyl, pollen, leaves, anthers, roots, root tips, pistil, petiole, flower, fruit, seed, stem and stalks of NUN 05004 SPS. In another preferred embodiment, the tissue culture does not contain somaclonal variation or has reduced somaclonal variation. The skilled person is familiar with methods to reduce somaclonal variation, including regular reinitiation.

In one embodiment the invention provides a Spinach plant regenerated from the tissue or cell culture of NUN 05004 SPS, wherein the regenerated plant is not significantly different from NUN 05004 SPS in all, or all but one, two or three, of the physiological and morphological characteristics (determined at the 5% significance level when grown under the same environmental conditions). Optionally, the plant has one, two or three the physiological and morphological characteristics that are affected by a mutation or by transformation. In another embodiment, the invention provides a Spinach plant regenerated from the tissue or cell culture of NUN 05004 SPS, wherein the plant has all of the physiological and morphological characteristics of said variety determined at the 5% significance level when grown under the same environmental conditions. In these cases, similarity or difference of a characteristic is determined by measuring the characteristics of a representative number of plants grown under the same environmental conditions, determining whether type/degree characteristics are the same or different and determining whether numerical characteristics are significantly different (determined at the 5% significance level).

A Spinach according to the invention, such as NUN 05004 SPS, or its progeny, or a plant having all physiological and/or morphological characteristics but one, two or three which are different from those of NUN 05004 SPS, can also be reproduced using vegetative reproduction methods. Therefore, the invention provides for a method of producing a plant, or a part thereof, of variety NUN 05004 SPS, comprising vegetative propagation of said variety. Vegetative propagation comprises regenerating a whole plant from a plant part of variety NUN 05004 SPS (or from a progeny of said variety or from or a plant having all physiological and/or morphological characteristics of said variety but one, two or three different characteristics), such as a cutting, a cell culture or a tissue culture.

The invention also concerns methods of vegetatively propagating a part of the plant of the invention NUN 05004 SPS. In certain embodiments, the method comprises the steps of: (a) collecting tissue or cells capable of being propagated from a plant of the invention; (b) cultivating said tissue or cells to obtain proliferated shoots; and (c) rooting said proliferated shoots, to obtain rooted plantlets. Steps (b) and (c) may also be reversed, i.e. first cultivating said tissue to obtain roots and then cultivating the tissue to obtain shoots, thereby obtaining rooted plantlets. The rooted plantlets may then be further grown, to obtain plants. In one embodiment, the method further comprises step (d) growing plants from said rooted plantlets. Therefore, the method also comprises regenerating a whole plant from said part of NUN 05004 SPS.

In a preferred embodiment, the part of the plant to be propagated is a cutting, a cell culture or a tissue culture.

The invention also provides for a vegetatively propagated plant of variety NUN 05004 SPS (or from progeny of said variety or from or a plant having all but one, two or three physiological and/or morphological characteristics of NUN 05004 SPS) wherein the plant has all of the morphological and physiological characteristics of NUN 05004 SPS when the characteristics are determined at the 5% significance level for plants grown under the same conditions. In another embodiment, the propagated plant has all but one, two or three of the morphological and physiological characteristics of NUN 05004 SPS when the characteristics are determined at the 5% significance level for plants grown under the same conditions. A part of said propagated plant or said propagated plant with one, two or three differences is also included.

In an embodiment, the invention provides a method for producing a Spinach plant, comprising the steps of:
  a. Growing a plant of claim 1 until it develop at least one leaf
  b. Collecting at least one leaf of step a)
Preferably, the leaf is collected at harvest maturity. In another embodiment, the leaf is collected at babyleaf stage. A plant of NUN 05004 SPS can be produced by seeding directly in the soil (e.g., field) or by germinating the seeds in controlled environment conditions (e.g., greenhouses) and optionally then transplanting the seedlings into the field. For example, the seed can be sown into prepared seed beds where they will remain for the entire production the crop.

In still another aspect the invention provides a method of producing a Spinach plant, comprising crossing a plant of Spinach NUN 05004 SPS with a second Spinach plant at least once, allowing seed to develop and optionally harvesting said progeny seed. The skilled person can select progeny from said crossing. Optionally, the progeny is crossed twice, thrice, or four, five, six or seven times, and allowed to set seed. In one embodiment of the invention, the first step in "crossing" comprises planting seeds of a first and a second parent Spinach plant, often in proximity so that pollination will occur; for example, mediated by insect vectors. Alternatively, pollen can be transferred manually. Where the plant is self-pollinated, pollination may occur without the need for direct human intervention other than plant cultivation. After pollination the plant can produce seed.

In yet another aspect the invention provides a method of producing a plant, comprising selfing a plant of variety NUN 05004 SPS one or more times, and selecting a progeny plant from said selfing. In one aspect the progeny plant retains all the distinguishing characteristics of NUN 05004 SPS described above. In a different embodiment the progeny plant comprises all (or all but one, two or three) of the physiological and morphological characteristic of NUN 05004 SPS of Table 1, and/or Table 2. In a further embodiment the progeny plant comprises all physiological and morphological characteristic of NUN 05004 SPS when grown under the same environmental conditions.

In other aspects, the invention provides a progeny plant of variety NUN 05004 SPS such as a progeny plant obtained by further breeding that variety. Further breeding with the variety of the invention includes selfing that variety one or more times and/or cross-pollinating that variety with another Spinach plant or variety one or more times. In particular, the invention provides for a progeny plant that retains all the essential morphological and physiological characteristics of NUN 05004 SPS or, in another embodiment, a progeny plant that retains all, or all but one, two or three, of the morphological and physiological characteristics of NUN 05004 SPS, optionally all or all but one, two or three of the characteristics as listed in Table 1 and/or 2, when grown under the same environmental conditions, determined at the 5% significance level for numerical characteristics. In a preferred embodiment, the progeny is a first generation progeny, i.e. the ovule or the pollen (or both) used in the crossing is an ovule or pollen of variety NUN 05004 SPS, i.e. the pollen comes from an anther of NUN 05004 SPS and the ovule comes from an ovary of NUN 05004 SPS. In another aspect, the invention provides for a vegetative reproduction of the variety and a plant having all, or all but 1, 2, or 3 of the physiological and morphological characteristics of NUN 05004 SPS (e.g. as listed in Table 1 and/or 2).

The morphological and/or physiological differences between two different individual plants of the invention (e.g. between NUN 05004 SPS and a progeny of NUN 05004 SPS) or between a plant of NUN 05004 SPS or progeny of said variety, or a plant having all, or all but 1, 2, or 3, of the physiological and morphological characteristics of NUN 05004 SPS (or all, or all but 1, 2, or 3 of the characteristics as listed in Table 1 and/or 2) and another known variety can easily be established by growing said variety next to each other or next to the other variety (in the same field, under the same environmental conditions), preferably in several locations which are suitable for said Spinach cultivation, and measuring morphological and/or physiological characteristics of a number of plants (e.g., to calculate an average value and to determine the variation range/uniformity within the variety). For example, trials can be carried out in Acampo Calif., USA (N 38 degrees 07'261"/W 121 degrees 18' 807", USA, whereby various characteristics, for example maturity, days from seeding to harvest, plant habit, plant attitude, leaf shape, leaf color, disease resistance, insect resistance, can be measured and directly compared for species of Spinach. Thus, the invention comprises Spinach plant having one, two or three physiological and/or morphological characteristics which are different from those of the plant of claim 1 and which otherwise has all the physiological and morphological characteristics of the plant of claim 1, when determined at the 5% significance level for plants grown under the same environmental conditions. In a preferred embodiment, the different characteristic is affected by a mutation or by transformation.

The morphological and physiological characteristics (and the distinguishing characteristics) of NUN 05004 SPS are provided in the Examples, in Table 1 and/or 2. Encompassed herein is also a plant obtainable from NUN 05004 SPS (e.g. by selfing and/or crossing and/or backcrossing with said variety and/or progeny of said variety) comprising all or all but one, two or three of the physiological and morphological characteristics of NUN 05004 SPS listed in Table 1 and/or 2 as determined at the 5% significance level for numerical characteristics or identical for non-numerical characteristics when grown under the same environmental conditions and/or comprising one or more (or all; or all except one, two or three) characteristics when grown under the same environmental conditions.

The morphological and/or physiological characteristics may vary somewhat with variation in the environment (such as temperature, light intensity, day length, humidity, soil, fertilizer use), which is why a comparison under the same environmental conditions is preferred. Colors can best be measured against The Munsell Book of Color (Munsell Color Macbeth Division of Kollmorgan Instruments Corporation) or using the Royal Horticultural Society Chart (World Wide Web at rhs.org.uk/Plants/RHS-Publications/RHS-colour-charts).

In yet a further embodiment, the invention provides for a method of producing a new Spinach plant. The method comprises crossing a plant of the invention i.e. NUN 05004 SPS, or a plant comprising all but 1, 2, or 3 of the morphological and physiological characteristics of said variety (as listed in Table 1 and/or 2), or a progeny plant thereof, either as male or as female parent, with a second Spinach plant (or a wild relative of Spinach) one or more times, and/or selfing a Spinach plant according to the invention i.e. NUN 05004 SPS, or a progeny plant thereof, one or more times, and selecting progeny from said crossing and/or selfing. The second Spinach plant may for example be a line or variety of the species line or variety of the species *Spinacia oleracea*, or other *Spinacia* species.

The invention provides for methods of producing plants which retain all the morphological and physiological characteristics of a plant of the invention i.e. NUN 05004 SPS. The invention provides also for methods of producing a plant comprising all but 1, 2, or 3 or more of the morphological and physiological characteristics of NUN 05004 SPS (e.g. as listed in Table 1 and/or 2), but which are still genetically closely related to said variety. The relatedness can, for example be determined by fingerprinting techniques (e.g., making use of isozyme markers and/or molecular markers such as Single-nucleotide polymorphism (SNP) markers, amplified fragment length polymorphism (AFLP) markers, microsatellites, minisatellites, Random Amplified Polymorphic DNA (RAPD) markers, restriction fragment length polymorphism (RFLP) markers and others). A plant is "closely related" to NUN 05004 SPS if its DNA fingerprint is at least 80%, 90%, 95% or 98% identical to the fingerprint of NUN 05004 SPS. In a preferred embodiment AFLP markers are used for DNA fingerprinting (Vos et al. 1995, Nucleic Acid Research 23: 4407-4414). A closely related plant may have a Jaccard's Similarity index of at least about 0.8, preferably at least about 0.9, 0.95, 0.98 or more (Parvathaneni et al., J. Crop Sci. Biotech. 2011 (March) 14 (1): 39~43).

The invention also provides a plant and a variety obtained or selected by applying these methods on NUN 05004 SPS. Such a plant may be produced by crossing and/or selfing, or alternatively, a plant may simply be identified and selected amongst plants of said variety, or progeny of said variety, e.g. by identifying a variant within NUN 05004 SPS or within progeny of said variety (e.g. produced by selfing) which variant differs from NUN 05004 SPS in one, two or three of the morphological and/or physiological characteristics (e.g. in one, two or three distinguishing characteristics), e.g. those listed in Table 1 and/or 2 or others. In one embodiment the invention provides a Spinach plant having a Jaccard's Similarity index with NUN 05004 SPS of at least 0.8, e.g. at least 0.85, 0.9, 0.95, 0.98 or even at least 0.99.

WO2013182646, which is incorporated by reference, relates to a non-destructive method for analyzing maternal DNA of a seed. In this method the DNA is dislodged from the seed coat surface and can be used to collect information on the genome of the maternal parent of the seed. This method for analyzing maternal DNA of a seed comprises the steps of contacting a seed with a fluid to dislodge DNA from the seed coat surface, and analyzing the DNA thus dislodged from the seed coat surface using methods known in the art. The skilled person is thus able to determine whether a seed has grown on a plant of a plant of the invention i.e. NUN 05004 SPS is a progeny of said variety, because the seed coat of the seed is a maternal tissue genetically identical to NUN 05004 SPS. In one embodiment, the present invention relates to a seed coat comprising maternal tissue of NUN 05004 SPS. In another embodiment the invention relates to a Spinach seed comprising a maternal tissue of NUN 05004 SPS.

By crossing and/or selfing also (one or more) single traits may be introduced into the variety of the invention i.e. NUN 05004 SPS (e.g., using backcrossing breeding schemes), while retaining the remaining morphological and physiological characteristics of said variety and/or while retaining one or more or all distinguishing characteristics. A single trait converted plant may thereby be produced. For example, disease resistance genes may be introduced, genes responsible for one or more quality traits, yield, etc. Both single genes (e.g. dominant or recessive) and one or more QTLs (quantitative trait loci) may be transferred into NUN 05004 SPS by breeding with said variety.

Alternatively, a single trait converted plant or single locus converted plant of NUN 05004 SPS may be produced by the following steps
  a. obtaining a cell or tissue culture of cells of NUN 05004 SPS;
  b. genetically transforming or mutating said cells;
  c. growing the cells into a plant; and
  d. optionally selecting a plant that contains the desired single locus conversion
The skilled person is familiar with various techniques for genetically transforming a single locus in a plant cell, or mutating said cells.

Any pest or disease resistance genes may be introduced into a plant according to the invention, i.e. NUN 05004 SPS, progeny of said variety or into a plant comprising all but 1, 2, or 3 or more of the morphological and physiological characteristics of NUN 05004 SPS (e.g. as listed in Table 1). Resistance to one or more of the following diseases or pests is preferably introduced into plants of the invention: *Peronospora farinose* fsp. *spinaciae*, e.g. to race 1-16 or new races and/or race 510C or other isolates; white rust (*Albugo occidentalis*), *Fusarium oxysporum* fsp. *spinaciae*, *Pythium* resistance, *Rhizoctonia* resistance, *Colletotrichum* anthracnose resistance, *Cercospora beticola* resistance, *Verticillium dahliae* resistance, *Phytophthora* ssp resistance, *Stemphylium* leaf spot resistance, Curly Top Virus resistance, Cucumber Mosaic Virus (CMV) resistance, Impatiens Necrotic Spot Virus (INSV), Beet Yellows and/or Beet mosaic resistance, leaf miner resistance. Other resistance genes, against pathogenic viruses, fungi, bacteria, nematodes, insects or other pests may also be introduced.

Thus, invention also provides a method for developing a Spinach plant in a Spinach breeding program, using a Spinach plant of the invention, or its parts as a source of plant breeding material. Suitable plant breeding techniques are recurrent selection, backcrossing, pedigree breeding, mass selection, mutation breeding and/or genetic marker enhanced selection. For example, in one aspect, the method comprises crossing NUN 05004 SPS or progeny of said variety, or a plant comprising all but 1, 2, or 3 or more of the morphological and physiological characteristics of NUN 05004 SPS (e.g. as listed in Table 1 and/or 2), with a different Spinach plant, and wherein one or more offspring of the crossing are subject to one or more plant breeding techniques selected from the group consisting of recurrent selection, backcrossing, pedigree breeding, mass selection, mutation breeding and genetic marker enhanced selection ((see e.g. Brotman et al., Theor Appl Genet (2002) 104: 1055-1063)). For breeding methods in general see Principles of Plant Genetics and Breeding, 2007, George Acquaah, Blackwell Publishing, ISBN-13: 978-1-4051-3646-4.

The invention also provides a Spinach plant comprising at least a first set of the chromosomes of Spinach variety NUN 05004 SPS, a sample of seed of said variety having been deposited under Accession Number NCIMB 43376; optionally further comprising a single locus conversion or a mutation, wherein said plant has essentially all of the morphological and physiological characteristics of the plant comprising at least a first set of the chromosomes of said variety. In another embodiment, this single locus conversion confers a trait selected from the group consisting of yield, storage properties, color, male sterility, herbicide tolerance, insect resistance, pest resistance, disease resistance, environmental stress tolerance, modified carbohydrate metabolism and modified protein metabolism.

In one embodiment, a plant according to the invention, i.e. NUN 05004 SPS may also be mutated (by e.g. irradiation, chemical mutagenesis, heat treatment, etc.) and mutated seeds or plants may be selected in order to change one or more characteristics of said variety. Methods such as TILLING may be applied to Spinach populations in order to identify mutants. Similarly, NUN 05004 SPS may be transformed and regenerated, whereby one or more chimeric genes are introduced into the variety or into a plant comprising all but 1, 2, 3, or more of the morphological and physiological characteristics (e.g. as listed in Table 1 and/or 2). Transformation can be carried out using standard methods, such as *Agrobacterium tumefaciens* mediated transformation or biolistics, followed by selection of the transformed cells and regeneration into plants. A desired trait (e.g. genes conferring pest or disease resistance, herbicide, fungicide or insecticide tolerance, etc.) can be introduced into NUN 05004 SPS, or progeny of said variety, by transforming said variety or progeny of said variety with a transgene that confers the desired trait, wherein the transformed plant retains all or all but one, two or three of the phenotypic and/or morphological and/or physiological characteristics of NUN 05004 SPS or the progeny of said variety and contains the desired trait.

The invention also provides a plant or a cell of a plant comprising a desired trait produced by mutating a plant of variety NUN 05004 SPS or a cell thereof and selecting a plant the desired trait, wherein the mutated plant retains all or all but one of the phenotypic and morphological characteristics of said variety, optionally as described for each variety in Table 1 and/or 2, and contains the desired trait and wherein a representative sample of seed of variety NUN 05004 SPS has been deposited under Accession Number NCIMB 43376. In a further embodiment, the desired trait is selected from the group consisting of yield, leaf shape, male sterility, herbicide tolerance, insect resistance, pest resistance, disease resistance, Powdery mildew resistance, environmental stress tolerance, modified carbohydrate metabolism, modified protein metabolism and ripening.

The invention also provides a plant having one, two or three physiological and/or morphological characteristics which are different from those of NUN 05004 SPS and which otherwise has all the physiological and morphological characteristics of said variety, wherein a representative sample of seed of variety NUN 05004 SPS has been deposited under Accession Number NCIMB 43376. In particular variants which differ from NUN 05004 SPS in none, one, two or three of the characteristics mentioned in Table 1 and/or 2 are encompassed.

A part of a variety of the invention, i.e. NUN 05004 SPS (or of progeny of said varieties or of a plant having all physiological and/or morphological characteristics but one, two or three which are different from those of said variety) encompasses any cells, tissues, organs obtainable from the seedlings or plants, such as but not limited to: a Spinach leaf or a part thereof, a cutting, hypocotyl, cotyledon, seed coat, pollen and the like. Such parts can be stored and/or processed further. Encompassed are therefore also food or feed products comprising a part of NUN 05004 SPS or a part of progeny of said varieties, or a part of a plant having all but one, two or three physiological and/or morphological characteristics of NUN 05004 SPS, comprising one or more of such parts, optionally processed (such as canned, chopped, cooked, roasted, in a sauce, in a sandwich, pasted, puréed or concentrated, juiced, frozen, dried, pickled, or powdered).

In one aspect a haploid plant and/or a doubled haploid plant of NUN 05004 SPS, or of a plant having all but one, two or three physiological and/or morphological characteristics of NUN 05004 SPS, or progeny of any of these, is encompassed herein. Haploid and doubled haploid (DH) plants can, for example, be produced by cell or tissue culture and chromosome doubling agents and regeneration into a whole plant. For DH production chromosome doubling may be induced using known methods, such as colchicine treatment or the like.

In yet another aspect haploid plants and/or doubled haploid plants derived from NUN 05004 SPS that, when combined, make a set of parents of NUN 05004 SPS are encompassed herein. Thus the haploid plant and/or the doubled haploid plant of NUN 05004 SPS can be used in a method for generating parental lines of NUN 05004 SPS.

Using methods known in the art like "reverse synthesis of breeding lines" or "reverse breeding", it is possible to produce parental lines for a hybrid plant such as NUN 05004 SPS; where normally the hybrid is produced from the parental lines. Thus, this method introduces a tool that was not available in traditional breeding: a skilled person can take any individual heterozygous plant (called a "phenotypically superior plant" in Example 2 of WO2014076249; NUN 05004 SPS is such a plant) and generate a combination of parental lines (reverse breeding parental lines) that, when crossed, produce the variety NUN 05004 SPS. It is not necessary that the reverse breeding parental lines are identical to the original parental lines. Such new breeding methods are based on the segregation of individual alleles in the spores produced by a desired plant and/or in the progeny derived from the self-pollination of that desired plant, and on the subsequent identification of suitable progeny plants in one generation, or in a limited number of inbred cycles. Such a method is known from WO2014076249 or from Nature Protocols Volume: 9, Pages: 761-772 (2014) DOI: doi: 10.1038/nprot.2014.049, which are enclosed by reference. Such method for producing parental lines for a hybrid organism, comprises the steps of: a) defining a set of genetic markers that are present in a heterozygous form (H) in a partially heterozygous starting organism; b) producing doubled haploid lines from spores of the starting organism: c) genetically characterizing the doubled haploid lines thus obtained for the said set of genetic markers to determine whether they are present in a first homozygous form (A) or in a second homozygous form (B); d) selecting at least one pair of doubled haploid lines that have complementary alleles for at least a subset of the genetic markers, wherein each member of the pair is suitable as a parental line for a hybrid organism.

Thus in one aspect, the invention relates to a method of producing a combination of parental lines of a plant of the invention (NUN 05004 SPS) comprising the step of making doubled haploid cells from haploid cells from said plant or a seed of that plant; and optionally crossing these parental lines to produce and collect seeds. In another aspect, the invention relates to a combination of parental lines produced by this method. In still another aspect said combination of parental lines can be used to produce a seed or plant of NUN 05004 SPS when these parental lines are crossed. In still another aspect, the invention relates to a combination of parental lines from which a seed or plant having all physiological and/or morphological characteristics of NUN 05004 SPS (when the characteristics are determined at the 5% significance level for plants grown under the same conditions).

In another aspect, the invention comprises a method for making doubled haploid cells from haploid cells of NUN 05004 SPS according to various methods known to the skilled person. A suitable method is colchicine treatment.

In another alternative aspect, the invention provides a method of introducing a single locus conversion or single trait conversion or a desired trait into NUN 05004 SPS comprising:
 a. obtain a combination of a parental lines of NUN 05004 SPS, optionally through reverse synthesis of breeding lines,
 b. introduce a single locus conversion in at least one of the parents of step a;
 c. crossing the converted parent with the other parent of step a to obtain seed of NUN 05004 SPS A combination of a male and a female parental line of NUN 05004 SPS can be generated by methods described herein, for example through reverse synthesis of breeding lines.

In an embodiment of the invention, Step b) of the above method—introduce a single locus conversion in at least one of the parents of step a—may be done through the following method:
 i. obtaining a cell or tissue culture of cells of the parental line of NUN 05004 SPS;
 ii. genetically transforming or mutating said cells;
 iii. growing the cells into a plant; and
 iv. optionally selecting plants that contain the single locus conversion, the single trait conversion or the desired trait.

In another embodiment of the invention, Step b) of the above method—introduce a single locus conversion in at least one of the parents of step a—may also be done through the following method:
 i. crossing the parental line of NUN 05004 SPS with a second Spinach plant comprising the single locus conversion, the single trait conversion or the desired trait;
 ii. selecting F1 progeny plants that contain the single locus conversion, the single trait conversion or the desired trait;
 iii. crossing said selected progeny plants of step ii with the parental line of step i, to produce a backcross progeny plant;
 iv. selecting backcross progeny plants comprising the single locus conversion, the single trait conversion or the desired trait and otherwise all or all but one, two or three of the morphological and physiological characteristics the parental line of step i to produce selected backcross progeny plants; and
 v. optionally repeating steps iii and iv one or more times in succession to produce selected second, third or fourth or higher backcross progeny plants comprising the single locus conversion, the single trait conversion or the desired trait and otherwise all or all but one, two or three of the morphological and physiological characteristics the parental line of step i to produce selected backcross progeny plants, when grown in the same environmental conditions.

The invention further relates to plants obtained by this method.

The above method is provided, wherein the single locus conversion concerns a trait, wherein the trait is yield or pest resistance or disease resistance. In one embodiment the trait is disease resistance and the resistance is conferred to *Peronospora farinose* fsp. *spinaciae*, e.g. to race 1-16 or new races and/or race 510C or other isolates; white rust (*Albugo occidentalis*), *Fusarium oxysporum* fsp. *spinaciae*, *Pythium* resistance, *Rhizoctonia* resistance, *Colletotrichum anthracnose* resistance, *Cercospora beticola* resistance, *Verticillium dahliae* resistance, *Phytophthora* ssp resistance, *Stemphylium* leaf spot resistance, Curly Top Virus resistance, Cucumber Mosaic Virus (CMV) resistance, Impatiens Necrotic Spot Virus (INSV), Beet Yellows and/or Beet mosaic resistance, leaf miner resistance. Other resistance genes, against pathogenic viruses, fungi, bacteria, nematodes, insects or other pests may also be introduced.

Thus, the invention also provides a combination of parental lines which, when crossed, produce a seed or plant having all physiological and/or morphological characteristics of NUN 05004 SPS but one, two or three which are different (when grown under the same environmental conditions), as well as a seed or plant having all physiological and/or morphological characteristics of NUN 05004 SPS but one, two or three which are different (when the characteristics are determined at the 5% significance level for plants grown under the same conditions).

Also provided is a plant part obtainable from variety NUN 05004 SPS or from progeny of said variety or from a plant having all but one, two or three physiological and/or morphological characteristics which are different from those of NUN 05004 SPS, or from a vegetatively propagated plant of NUN 05004 SPS (or from its progeny or from a plant having all or all but one, two or three physiological and/or morphological characteristics which are different from those of NUN 05004 SPS), being selected from the group consisting of a fruit, a harvested fruit, a part of a fruit, a leaf, a part of a leaf, pollen, an ovule, a cell, a petiole, a shoot or a part thereof, a stem or a part thereof, a root or a part thereof, a root tip, a cutting, a seed, a part of a seed, seed-coat or another maternal tissue which is part of a seed grown on NUN 05004 SPS, or hypocotyl, cotyledon, a scion, a stock, a rootstock, a pistil, an anther, and a flower or a part thereof.

In still yet another aspect, the invention provides a method of determining the genotype of a plant of the invention comprising the step of detecting in the genome (e.g., a sample of nucleic acids) of the plant at least a first polymorphism or an allele. The skilled person is familiar with many suitable methods of genotyping, detecting a polymorphism or detecting an allele including restriction fragment length polymorphism identification (RFLP) of genomic DNA, random amplified polymorphic detection (RAPD) of genomic DNA, amplified fragment length polymorphism detection (AFLP), polymerase chain reaction (PCR), DNA sequencing, allele specific oligonucleotide (ASO) probes, and hybridization to DNA microarrays or beads. Alternatively, the entire genome could be sequenced. The method may, in certain embodiments, comprise detecting a plurality of polymorphisms in the genome of the plant, for example by obtaining a sample of nucleic acid from a plant and detecting in said nucleic acids a plurality of polymorphisms. The method may further comprise storing the results of the step of detecting the plurality of polymorphisms on a computer readable medium The invention also provides for a food or feed product comprising or consisting of a plant part described herein wherein the plant part can be identified as a part of the plant of the invention. Preferably, the plant part is a Spinach leaf or part thereof and/or an extract from a leaf or another plant part described herein. The food or feed product may be fresh or processed, e.g., dried, grinded, powdered, pickled, chopped, cooked, roasted, in a sauce, in a sandwich, pasted, puréed or concentrated, juiced, pickled, canned, steamed, boiled, fried, blanched and/or frozen, etc.

Marketable Spinach leaves are generally sorted by size and quality after harvest.

All documents (e.g., patent publications) are herein incorporated by reference in their entirety.

CITED REFERENCES

Ren et al., In Vitro Cell. Dev. Biol.—Plant (2013) 49:223-229;
Colijn-Hooymans (1994), Plant Cell, Tissue and Organ Culture 39: 211-217
"Guidelines for the Conduct of Tests for Distinctness, Uniformity and Stability, TG104/5 (Geneva, last revised 2016), upov.int/under edocs/tgdocs/en/tg061.pdf
"Objective description of Variety Spinach *Spinacia oleracea* L.)", ST-470-83 the US Department of Agriculture, Agricultural Marketing Service, Plant Variety Protection Office, Beltsville, Md. 20705 world wide web at ams.usda.gov/under sites/default/files/media/83-Spinach%20ST-470-83%202015.pdf.
The Munsell Book of Color (Munsell Color Macbeth Division of Kollmorgan Instruments Corporation)
Royal Horticultural Society Chart (World Wide Web at rhs.org.uk/Plants/RHS-Publications/RHS-colour-charts).
(Vos et al. 1995, Nucleic Acid Research 23: 4407-4414).
(Parvathaneni et al., J. Crop Sci. Biotech. 2011 (March) 14 (1): 39-43).
WO2013182646,
Brotman et al., Theor Appl Genet (2002) 104:1055-1063
Principles of Plant Genetics and Breeding, 2007, George Acquaah, Blackwell Publishing, ISBN-13: 978-1-4051-3646-4.
WO2014076249;
Wijnker et al., Nature Protocols Volume: 9, Pages: 761-772 (2014) DOI: doi:10.1038/nprot.2014.049

Examples

Development of NUN 05004 SPS

The hybrid NUN 05004 SPS was developed from a male and female proprietary inbred line of Nunhems. The female and male parents were crossed to produce hybrid (F1) seeds of NUN 05004 SPS The seeds of NUN 05004 SPS can be grown to produce hybrid plants and parts thereof (e.g. Spinach fruit). The hybrid NUN 05004 SPS can be propagated by seeds or vegetative.

The hybrid variety is uniform and genetically stable. This has been established through evaluation of horticultural characteristics. Several hybrid seed production events resulted in no observable deviation in genetic stability. Coupled with the confirmation of genetic stability of the female and male parents the Applicant concluded that NUN 05004 SPS is uniform and stable.

DEPOSIT INFORMATION

A total of 2500 seeds of the hybrid variety NUN 05004 SPS were deposited according to the Budapest Treaty by Nunhems B.V. on Apr. 2, 2019, at the NCIMB Ltd., Ferguson Building, Craibstone Estate, Bucksburn, Aberdeen AB21 9YA, United Kingdom (NCIMB). The deposit has been assigned NCIMB number 43376. A deposit of NUN 05004 SPS and of the male and female parent line is also maintained at Nunhems B.V.

Access to the deposits will be available during the pendency of this application to persons determined by the Director of the U.S. Patent Office to be entitled thereto upon request. Subject to 37 C.F.R. § 1.808(b), all restrictions imposed by the depositor on the availability to the public of the deposited material will be irrevocably removed upon the granting of the patent. The deposit will be maintained for a period of 30 years, or 5 years after the most recent request, or for the enforceable life of the patent whichever is longer, and will be replaced if it ever becomes nonviable during that period. Applicant does not waive any rights granted under this patent on this application or under the Plant Variety Protection Act (7 USC 2321 et seq.).

The most similar variety to NUN 05004 SPS is referred to as Reference Variety, a variety from Nunhems with the commercial name Antalia. In Table 1 a comparison between NUN 05004 SPS and the Reference Variety is shown based on a trial in the USA. Trial location Acampo, Calif., USA, Fall trial: 15 Sep. 2016, winter trial: 17 Nov. 2016.

Two replications of 50 plants of each variety, from which 15 plants or plant parts were randomly selected, were used to measure characteristics. For numerical characteristics averages were calculated. For non-numerical characteristics the type/degree was determined. In Table 1 the USDA descriptors of NUN 05004 SPS (this application) and the Reference Variety (commercial variety) are listed.

In accordance with one aspect of the present invention, there is provided a plant having the physiological and morphological characteristics of NUN 05004 SPS as presented in Table 1.

TABLE 1

Objective description of varieties NUN 05004 SPS and Reference Variety

| USDA Descriptor | Application Variety NUN 05004 SPS | Reference Variety Antalia |
|---|---|---|
| PLOIDY; 1 = Diploid; 2 = tetraploid; 3 = other | 1 | 1 |
| MATURITY | | |
| Growth Rate: 1 = slow; 2 = medium (Long Standing Bloomsdale); 3 = fast (Dixie Market) | 2 | 2 |
| Days from planting to prime market stage | 36 | 36 |
| PLANT (Prime Market Stage): | | |
| Habit: 1 = flat (Viroflay); 2 = semi-erect (Long Standing Bloomsdale); 3 = erect (Virginia Savoy) | 2 | 1 |
| Size: 1 = small (America); 2 = medium; 3 = large (Giant Nobel) | 2 | 2 |
| Spread (cm) | 17.5 | 15.4 |
| Height (cm) | 11.9 | 10.5 |
| SEEDLING COTYLEDON | | |
| Width (mm) | 6.5 | 6.0 |
| Length (mm) | 6.1 | 4.1 |
| Tip: 1 = pointed; 2 = rounded | 2 | 2 |
| Color: 1 = light green; 2 = medium green; 3 = dark green; 4 = other | 1 | 2 |
| LEAF (First Foliage Leaves) | | |
| Shape: 1 = elliptic; 2 = circular; 3 = ovate; 4 = other | 3 | 3 |
| Base: 1 = V-base; 2 = straight; 3 = lobed | 1 | 1 |
| Tip: 1 = round; 2 = round-pointed; 3 = pointed | 1 | 1 |
| Margin: 1 = flat; 2 = slightly curled; 3 = curled under | 2 | 2 |
| Upper Surface Color: 1 = light green (Hollandia); 2 = medium green (Giant Nobel); 3 = dark green (Long Standing Bloomsdale) | 2 (RHS Yellow green 146 B) | 3 (RHS Yellow green 146 A) |
| Lower Surface Color: 1 = lighter; 2 = same; 3 = darker | 2 (RHS Yellow green 146 B) | 2 (RHS Yellow green 146 A) |
| LEAF (Prime Market Stage) | | |
| Surface: 1 = smooth (Viroflay); 2 = semi-savoy (Northland); 3 = savoy (Virginia Savoy) | 2 | 2 |
| Shape: 1 = elliptic; 2 = circular; 3 = ovate; 4 = three sided; 5 = five-sided; 6 = arrow-shaped; 7 = asymmetrical | 6 | 3 |
| Base: 1 = V-base; 2 = straight; 3 = lobed | 3 | 3 |
| Tip: 1 = round; 2 = round-pointed; 3 = pointed | 1 | 1 |
| Margin: 1 = flat; 2 = slightly curled; 3 = curled under; 4 = curled up | 2 | 2 |
| Upper Surface Color: 1 = light green (Hollandia); 2 = medium green (Giant Nobel); 3 = dark green (Long Standing Bloomsdale); 4 = dull green (Northland) | 3 (RHS Green 137 A) | 3 (RHS Green 137 B) |
| Lower Surface Color: 1 = lighter; 2 = same; 3 = darker | 1 (RHS Green 137 B) | 2 (RHS Yellow green 146 B) |
| Luster: 1 = glossy; 2 = dull | 1 | 1 |
| Blade Size: 1 = small (Long Standing Bloomsdale); 2 = medium (Virginia Savoy); 3 = large (Giant Nobel) | 2 | 1 |
| Blade Lobing: 1 = not lobed; 2 = lobed | 2 | 2 |
| Petiole Color: 1 = white; 2 = light yellow; 3 = light green; 4 = medium green | 4 (RHS Yellow green 146 B) | 4 (RHS Yellow green 146 B) |
| Petiole Red Pigmentation: 1 = present; 2 = absent | 2 | 2 |
| Petiole Length to the Blade (mm) | 4 | 2 |
| Petiol Length: 1 = short; 2 = medium; 3 = long (Viroflay) | 2 | 1 |
| Petiole Diameter (mm) | n.r. | n.r. |
| Petiole Diameter: 1 = small; 2 = medium; 3 = large (Giant Nobel) | 2 | 2 |
| SEED STALK DEVELOPMENT | | |
| Start of Bolting (10% of plants): 1 = Early (Dixie Market); 2 = Medium (Long Standing Bloomsdale); 3 = Late (Norgreen) | 2 | 3 |
| Height of Stalk (cm) | 48.4 | 42.7 |
| Leaves on Stalk of Female Plant: 1 = Few or None; 2 = Many | 2 | 2 |
| Leaves on Stalk of Male Plant: 1 = Few or None; 2 = Many | 2 | 2 |
| Plants that are Female: 1 = 0-10%; 2 = 11-35%; 3 = 36-65%; 4 = 66-90%; 5 = 91-100% | n.r. | n.r. |
| Plants that are Male: 1 = 0-10%; 2 = 11-35%; 3 = 36-65%; 4 = 66-90%; 5 = 91-100% | n.r. | n.r. |
| Plants that are Monoecious: 1 = 0-10% 2 = 11-35% 3 = 36-65% 4 = 66-90% 5 = 91-100% | n.r. | n.r. |
| SEED: | | |
| Surface: 1 = Smooth; 2 = Prickly | 1 | 1 |

| Technical data of variety for observing several trials | | |
|---|---|---|
| Main expression of the characteristics | Type | Application Variety NUN 05004 SPS |
| main use of the candidate variety | | Fresh market/organic and conventional world wide |
| Conditions of cultivation for the observation and measurement of characteristics | Place cultivation | |

Technical data of variety for observing several trials

| Main expression of the characteristics | Type | Application Variety NUN 05004 SPS |
|---|---|---|
| | Period and year/months of cultivation | Summer, Spring, Autumn |
| | Methods of cultivation (i.e. open field, facilities, direct planting, potting, number of plants etc. | Open field and tunnels |
| Seedling: length of cotyledon | 3 short/5 medium/7 long | 3 |
| Leaf: anthocyanin coloration of petioles and veins | 1 absent/9 present | 1 |
| Leaf blade: intensity of green color | 1 very light/2 very light to light/3 light/4 light to medium/5 medium/ 6 medium to dark/7 dark/8 dark to very dark/9 very dark | 4 |
| Leaf blade: blistering | 1 absent or very weak/2 very weak to weak/3 weak/4 weak to medium/ 5 medium/6 medium to strong/ 7 strong/8 strong to very strong/9 very strong | 5 |
| Leaf blade: lobing | 1 absent or very weak/3 weak/5 medium/7 strong | 1 |
| Petiole: attitude | 1 erect/3 semi erect/5 horizontal | 3 |
| Petiole: length | 1 very short/3 short/5 medium/ 7 long/9 very long | 5 |
| Leaf blade: attitude | 1 erect/3 semi erect/5 horizontal/ 7 semi-pendulous | 3 |
| Leaf blade: shape (excluding basal lobes) | 1 triangular/2 medium ovate/ 3 broad ovate/4 medium elliptic/ 5 broad elliptic/6 circular | 3 |
| Leaf blade: curving of margin | 1 incurved/2 flat/3 recurved | 3 |
| Leaf blade: shape of apex | 1 acute/2 obtuse/3 rounded | 3 |
| Leaf blade: shape in longitudinal section | 1 concave/2 flat/3 convex | 2 |
| Proportion of monoecious plants | 1 absent or very low/2 very low to low/3 low/4 low to medium/ 5 medium/6 medium to high/7 high/ 8 high to very high/9 very high % | 9 100 |
| Proportion of female plants | 1 absent or very low/2 very low to low/3 low/4 low to medium/5 medium/6 medium to high/7 high/ 8 high to very high/9 very high | 1 |
| Proportion of male plants | 1 absent or very low/2 very low to low/3 low/4 low to medium/5 medium/6 medium to high/7 high/ 8 high to very high/9 very high | 1 |
| Time of start of bolting (for spring sown crops, 15% of plants) | 1 very early/2 very early to early/ 3 early/4 early to medium/ 5 medium/6 medium to late/7 late/ 8 late to very late/9 very late ±comparable with the variety | 5 Antalia |
| Seed: spines (harvest seed) | 1 absent/9 present | 1 |
| Type of culture | 1 in glasshouse/2 in the open/ 3 in the open and in the glasshouse | 2 |
| Growing season | 1 spring; please mention 1 if growing season is spring. | 1 |
| Growing season | 3 autumn; please mention 3 if growing season is autumn | 3 |
| main use | 1 fresh market/2 canning/3 ornamental | 1 |

Table 1 and 2 contain typical values. Values may vary due to environment. Other values that are substantially equivalent are also within the scope of the invention. N.A.=not applicable; n.r.=not recorded.

What is claimed is:

1. A hybrid plant, plant part or seed of Spinach variety NUN 05004 SPS, wherein a representative sample of seed of said spinach variety NUN 05004 SPS is deposited under Accession Number NCIMB 43376.

2. The plant part of claim 1, wherein the plant part is a leaf, pollen, an ovule, a fruit, a scion, a root, a rootstock, cutting, flower or a part of any of these or a cell.

3. A seed that produces the plant of claim 1.

4. A seed grown on the plant of claim 1.

5. A Spinach plant or a part thereof having all of the physiological and morphological characteristics listed in Table 1, when the characteristics are determined at the 5% significance level for plants grown under the same environmental conditions, and wherein a representative sample of seed of said spinach variety NUN 05004 SPS is deposited under Accession Number NCIMB 43376.

6. A Spinach plant or a part thereof which does not differ from the plant of NUN 05004 SPS, when the characteristics are determined at the 5% significance level when grown under the same environmental conditions, and wherein a representative sample of seed of said spinach variety NUN 05004 SPS is deposited under Accession Number NCIMB 43376.

7. A tissue or cell culture comprising cells or protoplasts derived from a plant part of NUN 05004 SPS, wherein a representative sample of seed of said spinach variety NUN 05004 SPS is deposited under Accession Number NCIMB 43376, and wherein said plant part is a meristem, a cotyledon, a hypocotyl, pollen, a leaf, an anther, a root, a root tip, a pistil, a petiole, a flower, a fruit, a stem, or a stalk.

8. A Spinach plant regenerated from the tissue or cell culture of claim 7, wherein the plant has all of the physiological and morphological characteristics of the plant of NUN 05004 SPS, when the characteristics are determined at the 5% significance level for plants grown under the same environmental conditions, and wherein a representative sample of seed of spinach variety NUN 05004 SPS is deposited under Accession Number NCIMB 43376.

9. A method of producing the plant of claim 1, said method comprising vegetative propagation of at least a part of NUN 05004 SPS, wherein a representative sample of seed of said spinach variety NUN 05004 SPS is deposited under Accession Number NCIMB 43376.

10. The method of claim 9, wherein said vegetative propagation comprises regenerating a whole plant from said part of NUN 05004 SPS, wherein a representative sample of seed of said spinach variety NUN 05004 SPS is deposited under Accession Number NCIMB 43376.

11. The method of claim 9, wherein said part is a cutting.

12. A vegetative propagated plant of NUN 05004 SPS or a part thereof, wherein the vegetative propagated plant has all of the physiological and morphological characteristics of the plant of NUN 05004 SPS, when the characteristics are determined at the 5% significance level for plants grown under the same environmental conditions, and wherein a representative sample of seed of spinach variety NUN 05004 SPS is deposited under Accession Number NCIMB 43376.

13. A method of producing a Spinach plant, said method comprising crossing the plant of claim 1 with a second Spinach plant at least once, and selecting progeny from said crossing.

14. A Spinach plant having one physiological or morphological characteristic which is different from those of the plant of claim 1 and which otherwise has all the physiological and morphological characteristics of the plant of claim 1, when determined at the 5% significance level for plants grown under the same environmental conditions.

15. The plant of claim 1, further comprising a single locus conversion, wherein said plant has all of the morphological and physiological characteristics of the plant of NUN 05004 SPS, wherein a representative sample of seed of said spinach variety NUN 05004 SPS is deposited under Accession Number NCIMB 43376, when said characteristics are determined at the 5% significance level for plants grown under the same environmental conditions, and wherein the single locus conversion confers a trait selected from the group consisting of male sterility, herbicide tolerance, insect resistance, pest resistance, disease resistance, environmental stress tolerance, modified carbohydrate metabolism and modified protein metabolism.

16. A method of producing double haploids of NUN 05004 SPS comprising making doubled haploid cells made from haploid cells from the plant or seed of NUN 05004 SPS, wherein a representative sample of seed of spinach variety NUN 05004 SPS is deposited under Accession Number NCIMB 43376.

17. A container comprising the plant, plant part or seed of claim 1.

18. A food, a feed product or a processed product comprising the plant part of claim 2.

19. A method of producing a Spinach leaf, comprising:
   a. growing a plant of claim 1 until it develops at least one leaf; and
   b. collecting the leaf of step a).

* * * * *